(12) United States Patent
Hasegawa et al.

(10) Patent No.: US 11,109,834 B2
(45) Date of Patent: Sep. 7, 2021

(54) ULTRASONIC IMAGE PICKUP APPARATUS

(71) Applicant: HITACHI, LTD., Tokyo (JP)

(72) Inventors: Hiroaki Hasegawa, Tokyo (JP); Hiroki Tanaka, Tokyo (JP)

(73) Assignee: Hitachi, Ltd., Tokyo (JP)

(*) Notice: Subject to any disclaimer, the term of this patent is extended or adjusted under 35 U.S.C. 154(b) by 341 days.

(21) Appl. No.: 15/938,525

(22) Filed: Mar. 28, 2018

(65) Prior Publication Data

US 2018/0279990 A1   Oct. 4, 2018

(30) Foreign Application Priority Data

Feb. 28, 2017 (JP) .............................. JP2017-037254

(51) Int. Cl.
*A61B 8/14* (2006.01)
*A61B 8/00* (2006.01)
(Continued)

(52) U.S. Cl.
CPC .............. *A61B 8/14* (2013.01); *A61B 8/5207* (2013.01); *A61B 8/54* (2013.01); *B06B 1/0292* (2013.01);
(Continued)

(58) Field of Classification Search
CPC ........... A61B 8/14; A61B 8/54; A61B 8/5207; A61B 8/4483; A61B 8/485; A61B 8/4281;
(Continued)

(56) References Cited

U.S. PATENT DOCUMENTS 8,315,125 B2 * 11/2012 Lemmerhirt ........... G01H 11/06
367/140
10,603,012 B2   3/2020 Gemma et al.
(Continued)

FOREIGN PATENT DOCUMENTS

JP   2013/126069 A    6/2013
JP   2016/202327 A   12/2016
WO  2005/120359 A1   12/2005

OTHER PUBLICATIONS

Park et al. 2013 IEEE Trans. Ultrason. Ferroelec. Freq. Cont. 60:1245-1255 (Year: 2013).*
(Continued)

*Primary Examiner* — Michael J Tsai
*Assistant Examiner* — Patrick M Mehl
(74) *Attorney, Agent, or Firm* — Mattingly & Malur, PC

(57) ABSTRACT

The ultrasonic image pickup apparatus includes a transmission/reception control unit that transmits an ultrasonic wave by applying a DC bias voltage and an AC driving voltage between electrodes of the electrostatic capacity type micromachined ultrasonic transducer and picks up an image by transmitting and receiving two or more kinds of ultrasonic waveforms which have different signs, amplitudes, or phases from each other for one scanning line. In addition, as the AC driving voltage, the ultrasonic image pickup apparatus uses a voltage waveform that is obtained by adding a high frequency pulse waveform and a low frequency waveform that has a longer cycle than that of the high frequency pulse waveform and has such a voltage amplitude as makes the total voltage of the low frequency waveform and the DC bias voltage is equal or smaller than a pull-in voltage.

14 Claims, 7 Drawing Sheets

(51) Int. Cl.
  *G01S 7/52* (2006.01)
  *B06B 1/02* (2006.01)
  *G01S 15/89* (2006.01)
  *A61B 8/08* (2006.01)

(52) U.S. Cl.
  CPC ........ *G01S 7/5202* (2013.01); *G01S 7/52038* (2013.01); *G01S 15/8915* (2013.01); *A61B 8/4483* (2013.01); *B06B 1/0207* (2013.01)

(58) Field of Classification Search
  CPC ........... A61B 8/00; A61B 8/4488; A61B 8/12; A61B 2562/028; G01S 7/52038; G01S 7/5202; G01S 15/8915; G01S 15/895; G01S 15/8963; G01S 15/8979; G01S 7/52026; G01S 15/8913; B06B 1/0292; B06B 1/0207; G10K 9/121
  See application file for complete search history.

(56) References Cited

U.S. PATENT DOCUMENTS

| | | | |
|---|---|---|---|
| 2005/0219953 A1* | 10/2005 | Bayram | B06B 1/0292 367/178 |
| 2007/0083119 A1* | 4/2007 | Adachi | A61B 8/00 600/437 |
| 2010/0168575 A1* | 7/2010 | Hashiba | G01S 15/8963 600/443 |
| 2013/0331699 A1* | 12/2013 | Ishihara | G01S 7/52038 600/443 |
| 2014/0150556 A1* | 6/2014 | Angelsen | G01S 7/52077 73/627 |

OTHER PUBLICATIONS

Japanese Office Action received in corresponding Japanese Application No. 2017-037254 dated Jul. 7, 2020.

\* cited by examiner

ULTRASONIC IMAGE PICKUP APPARATUS

TECHNICAL FIELD

The present invention relates to an ultrasonic image pickup apparatus and, more particularly, relates to an ultrasonic image pickup apparatus using an electrostatic capacity type micro-machined ultrasonic transducer as an ultrasonic probe.

BACKGROUND ART

Patent Literature 1 discloses a technology in which a DC bias signal with a constant cycle is superimposed on a high frequency pulse signal, the high frequency signal is applied to electrostatic capacity type ultrasonic vibrators, and the voltage value of the DC bias signal is adjusted, so that a high sound pressure is obtained.

CITATION LIST

Patent Literature

Patent Literature 1: WO 2005/120359

SUMMARY OF INVENTION

Technical Problem

As an example of an ultrasonic image pickup apparatus, there is an ultrasonic image pickup apparatus that uses an electrostatic capacitor type micro-machined ultrasonic transducer as an ultrasonic probe. In the recent image diagnosis of superficial tissues using such an ultrasonic image pickup apparatus, it is indispensable to obtain high-resolution images using THI (Tissue Harmonic Imaging), and in order to realize this, it becomes necessary to improve the S/Ns (Signal to Noise ratios) of images.

For example, although, in the technology disclosed in the abovementioned Patent Literature 1, a high frequency pulse signal, on which a DC bias signal is superimposed, is applied to an ultrasonic vibrator, this technology is not suitable for realizing the S/N improvement of images using high sound pressures because the movable range of a vibration film is not fully utilized.

One object of the present invention is to provide an ultrasonic image pickup apparatus that realizes the S/N improvement of images with the use of high sound pressures.

The abovementioned object and other objects of the present invention and the new characteristics of the present invention will be explicitly shown by the following descriptions of the present specification and the accompanying drawings.

Solution to Problem

The outline of a representative one of inventions disclosed in the present application is as follows if summarized simply.

An ultrasonic image pickup apparatus according to an embodiment is an ultrasonic image pickup apparatus using an electrostatic capacity type micro-machined ultrasonic transducer as an ultrasonic probe. This ultrasonic image pickup apparatus includes a transmission/reception control unit that transmits an ultrasonic wave by applying a DC bias voltage and an AC driving voltage between electrodes of the electrostatic capacity type micro-machined ultrasonic transducer and picks up an image by transmitting and receiving two or more kinds of ultrasonic waveforms which have different signs, amplitudes, or phases from each other for one scanning line. And the ultrasonic image pickup apparatus uses a voltage waveform that is obtained by adding a high frequency pulse waveform and a low frequency waveform that has a longer cycle than that of the high frequency pulse waveform and has such a voltage amplitude as makes the total voltage of the low frequency waveform and the DC bias voltage equal or smaller than a pull-in voltage, and that smoothly changes in accordance with an arbitrary function as the AC driving voltage for at least one kind of transmission ultrasonic wave of the two or more kinds of the transmission ultrasonic waves. For example, it is preferable that a trapezoidal wave, a cosine function, an nth power of cosine, a Gaussian function or the like should be used as the arbitrary function.

Another ultrasonic image pickup apparatus according to an embodiment is an ultrasonic image pickup apparatus using an electrostatic capacity type micro-machined ultrasonic transducer as an ultrasonic probe. This ultrasonic image pickup apparatus includes a transmission/reception control unit that transmits two transmission waveforms respectively through two transmissions to the electrostatic capacitor type micro-machined ultrasonic transducer in which at least one of the two transmission waveforms has a low frequency component superimposed thereon. Furthermore, the voltage component of the low frequency component is a voltage used for adjusting the initial position of the vibration film of the electrostatic capacitor type micro-machined ultrasonic transducer.

Advantageous Effects of Invention

An advantageous effect obtained by the representative one of inventions disclosed in the present application is as follows if explained simply.

According to an embodiment, the S/N improvement of images can be realized with the use of high sound pressures.

DESCRIPTION OF EMBODIMENTS

Figure 1:
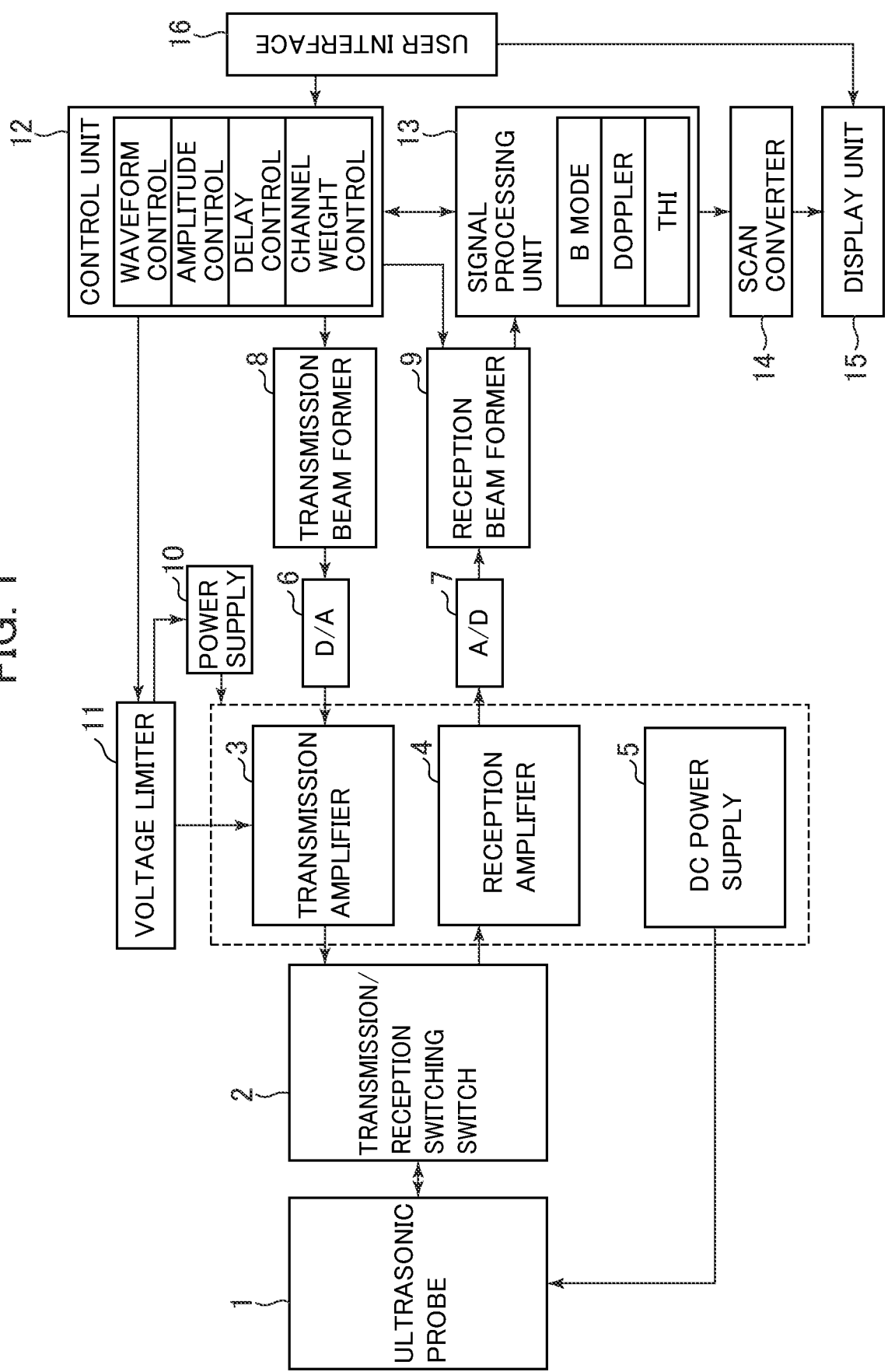
FIG. 1 is a block diagram showing an example of the configuration of an ultrasonic image pickup apparatus according to an embodiment.

Hereinafter, an embodiment will be explained with reference to the accompanying drawings. Through all drawings used for explaining the embodiment, the same components are given the same reference signs in principle, and redundant explanations about the same components will be omitted. In addition, in order to make the drawings easy to understand, there is a case of hatching a drawing even if the drawing is a plan view, and there is also a case of not hatching a drawing even if the drawing is a cross-sectional view.

Embodiment

The embodiment will be explained with reference to FIG. 1 to FIG. 9. This embodiment is an ultrasonic image pickup apparatus that uses an electrostatic capacitor type micro-machined ultrasonic transducer (CMUT) as an ultrasonic probe. In the following descriptions, there are cases where the electrostatic capacitor type micro-machined ultrasonic transducer is simply written as the ultrasonic transducer or the CMUT.

<Ultrasonic Image Pickup Apparatus>

First, the ultrasonic image pickup apparatus according to this embodiment will be explained with reference to FIG. 1. FIG. 1 is a block diagram showing an example of the configuration of the ultrasonic image pickup apparatus according to the embodiment.

As shown in FIG. 1, the ultrasonic image pickup apparatus includes: an ultrasonic probe 1; a transmission/reception switching switch 2; a transmission amplifier 3; a reception amplifier 4; a DC power supply 5; a D/A converter 6; an A/D converter 7; a transmission beam former 8; a reception beam former 9; a power supply 10; a voltage limiter 11; a control unit 12; a signal processing unit 13; a scan converter 14; a display unit 15; and a user interface 16.

The ultrasonic image pickup apparatus uses an ultrasonic transducer (refer to FIG. 2 and FIG. 3 to be hereinafter described) as the ultrasonic probe 1. The ultrasonic probe 1 is connected to the transmission beam former 8 and the reception beam former 9 of the ultrasonic image pickup apparatus including this ultrasonic probe 1 via the transmission/reception switching switch 2. The ultrasonic probe 1 operates as an array that forms an ultrasonic beam in cooperation with the DC power supply 5, the transmission amplifier 3, and the reception amplifier 4 that are driven by the power supply 10, and the ultrasonic probe 1 is used for transmitting/receiving ultrasonic waves. Transmission and reception signals are controlled by the control unit 12 in accordance with the aims of the transmission and reception.

The waveform of the transmission signal is controlled by the control unit 12, and the voltage of the transmission signal is applied to respective cells or to the electrodes of a channel composed of bundled cells via the transmission beam former 8, the D/A converter 6, and transmission amplifier 3 in such a way that an arbitrary waveform, an arbitrary amplitude, and an arbitrary delay time are set to the voltage of the transmission signal. Furthermore, the voltage limiter 11 is provided lest an excess voltage should be applied to the ultrasonic probe 1, or for the purpose of transmission waveform control. The reception signal is converted into an image signal via B mode cross-sectional image processing, Doppler processing, THI processing, or the like in the signal processing 13 after the reception signal goes through the reception amplifier 4, the A/D converter 7, and the reception beam former 9, and the image signal is displayed on the display unit 15 via the scan converter 14. Alternatively, it is conceivable that some of the components shown in FIG. 1 is realized as some of components inside the ultrasonic probe 1.

Hereinafter, the flow from the transmission/reception of ultrasonic wave signals to the image display will be explained. Generally speaking, the ultrasonic image pickup apparatus displays the structure of a living organism two-dimensionally or three-dimensionally. Therefore, in the case of the transmission or reception of ultrasonic waves, with the use of the array type ultrasonic probe 1, an electrical delay operation is performed on each channel or the number of channels to be used is set, beam forming is executed, and images are picked up by scanning the focuses of the ultrasonic waves two-dimensionally or three-dimensionally. These operations are performed inside the transmission beam former 8 or the reception beam former 9. In addition, control over the beam formers is executed in the control unit 12 in accordance with various image pickup modes.

In the case of transmission, voltages are applied to the respective channels, which are controlled by the transmission beam former 8, inside the ultrasonic probe 1 via the transmission amplifier 3, and ultrasonic waves radiated from the respective channels are transmitted so that the respective ultrasonic waves become in phase at a certain focus. The transmission and the reception are alternately conducted using the same ultrasonic probe 1, therefore it is necessary to switch the transmission and the reception using the transmission/reception switching switch 2.

In the case of reception, reception signals are amplified by the reception amplifier 4, and after going through the reception beam former 9, the signals are detected by the signal processing unit 13. In the signal processing unit 13, the respective signals are added while the phases thereof are being aligned, and after filter processing, logarithmic compression, wave detection, and the like are performed on the signals, the signals are converted into two-dimensional image data or three-dimensional image data corresponding to sound field scanning before scanning conversion. This image data is scan-converted by the scan converter 14, and output to the display unit 15 as image signals. The above-described control by the control unit 12 and the above-described adjustment of the display unit 15 can be executed by a user via the user interface 16.

The ultrasonic image pickup apparatus according to this embodiment includes the control unit 12 and a transmission/reception control unit including the transmission beam former 8 and the reception beam former 9. In this transmission/reception control unit, an ultrasonic wave is transmitted by applying a DC bias voltage and an AC driving voltage between the electrodes of an ultrasonic transducer, and picks up an image by transmitting and receiving two or more kinds of ultrasonic waveforms which have different signs, amplitudes, or phases from each other for one scanning line, although the detail of the above behavior of the transmission/reception control unit will be described later.

<Ultrasonic Transducer>

Figure 2:
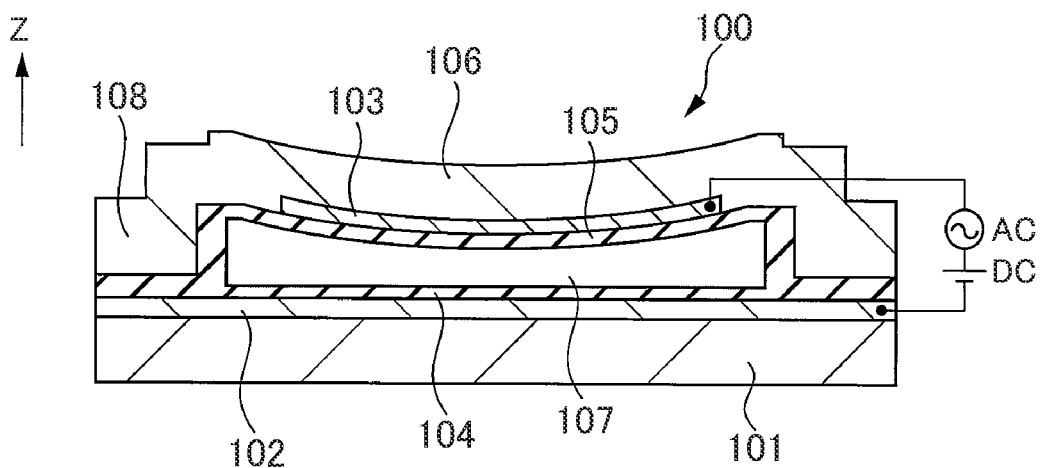
FIG. 2 is a vertical cross-sectional view showing an example of the structure of an ultrasonic transducer used for the ultrasonic image pickup apparatus according to the embodiment.

Next, the ultrasonic transducer used in the ultrasonic image pickup apparatus according to this embodiment will be explained with reference to FIG. 2 and FIG. 3. FIG. 2 is a vertical cross-sectional view showing an example of the structure of the ultrasonic transducer. FIG. 2 shows one of the elements (CMUT cell) of a CMUT which is an ultrasonic transducer.

As shown in FIG. 2, an ultrasonic transducer (CMUT cell) 100 includes: a substrate 101; a fixed electrode 102; a movable electrode 103; an insulating film 104; an insulating film 105; a diaphragm layer 106; a void layer 107; and a supporting wall 108. Because the diaphragm 106 functions as the vibration film of the ultrasonic transducer 100, it is also referred to as the vibration film 106.

In the ultrasonic transducer 100, the filmy fixed electrode 102 composed of conductive material such as aluminum, tungsten, or titanium is formed on the flat-plate substrate 101 composed of semiconductor or insulating material such as single crystal silicon, quartz glass, or polymer, and the diaphragm layer 106 is formed over the fixed electrode 102. The periphery of the diaphragm layer 106 is fixed to the substrate 101 by the supporting wall 108 which is extending up from the substrate 101, and the void layer 107, the periphery of which is hermetically sealed by the supporting wall 108, is formed between the diaphragm layer 106 and the substrate 101. The movable electrode 103, which is covered with the insulating film 105, is disposed over the void layer 107, and the movable electrode 103 resides inside the diaphragm layer 106.

When a voltage (a DC bias voltage DC plus an AC voltage AC) is applied between the fixed electrode 102 and the movable electrode 103, the movable electrode 103 is displaced toward the substrate 101 by an electrostatic force. It is preferable that the insulating film 104 should be installed on the fixed electrode 102 or the movable electrode 103 should be covered with the insulating film 105 lest the movable electrode 103 should come into contact with the fixed electrode 102 and both electrodes should be electrically conducted with each other when this displacement becomes excessive. Here, there might be various shapes of the elements of the ultrasonic transducer 100 depending on designs for meeting the needs of the specification such as a shape in which the movable electrode 103 protrudes outside the diaphragm layer 106, a shape in which the movable electrode 103 reaches the supporting wall 108, or a shape in which the thickness of the diaphragm layer 106 is not constant.

The movable electrode 103, which is covered by the diaphragm layer 106, the supporting wall 108, and the insulating film 105, is made of material that can be processed by a semiconductor process technology. For example, such material is silicon, sapphire, any type of glass material, polymer (polyimide, etc.), polycrystalline silicon, silicon nitride, acid silicon nitride, metallic thin film (aluminum alloy thin film, copper alloy thin film, tungsten thin film, etc.), spin-on-glass (SOG), implanted doping material or diffused doping material, or laminated film including oxide silicon, silicon nitride, and the like. The inside of the void layer 107 can be vacuum, or can be filled with air or any kind of gas. In the steady (non-operational) state, a distance between the movable electrode 103 and the substrate 101 (in the Z axis direction) is kept as it is mainly by the rigidities of the diaphragm, layer 106, the supporting wall 108, and the movable electrode 103.

The ultrasonic transducer 100 operates as a variable-capacitance capacitor having the fixed electrode 102 and the movable electrode 103 with the void layer 107 and the insulating film 104 therebetween. If the movable electrode 103 is displaced in the Z axis direction at the time a force is applied to the movable electrode 103, the distance between the fixed electrode 102 and the movable electrode 103 changes, hence the electrostatic capacitance of the capacitor changes. Because the movable electrode 103 and the diaphragm layer 106 are tightly connected to each other, if a force is applied to the diaphragm layer 106, the movable electrode 103 is also displaced. In this case, if an electric charge is accumulated between the fixed electrode 102 and the movable electrode 103, because the distance between the fixed electrode 102 and the movable electrode 103 changes, the electrostatic capacitance between both electrodes changes, and at the same time, a voltage occurs between both electrodes. In such a way, a force that brings about a mechanical displacement of some kind such as an ultrasonic wave is propagated to the diaphragm 106, and the displacement is converted into an electrical signal.

In addition, when various potential differences are given between the fixed electrode 102 and the movable electrode 103, various electric charges with different signs are accumulated, and the movable electrode 103 is variously displaced in the Z axis direction by electrostatic forces. In this case, because the movable electrode 103 and the diaphragm layer 106 are tightly connected to each other, the diaphragm 106 is also displaced at the same time. Therefore, if a sound propagation medium such as air, water, plastic, rubber, a living organism, or the like resides over the diaphragm 106 (in the Z axis direction), sounds are radiated. In other words, this ultrasonic transducer 100 is an electro-acoustic transducing device that has a function of: transducing an input signal into an ultrasonic wave signal, radiating the ultrasonic wave signal to a medium adjacent to the diaphragm layer 106; transducing an ultrasonic wave signal input from the medium into an electric signal; and outputting the electric signal.

Figure 3:
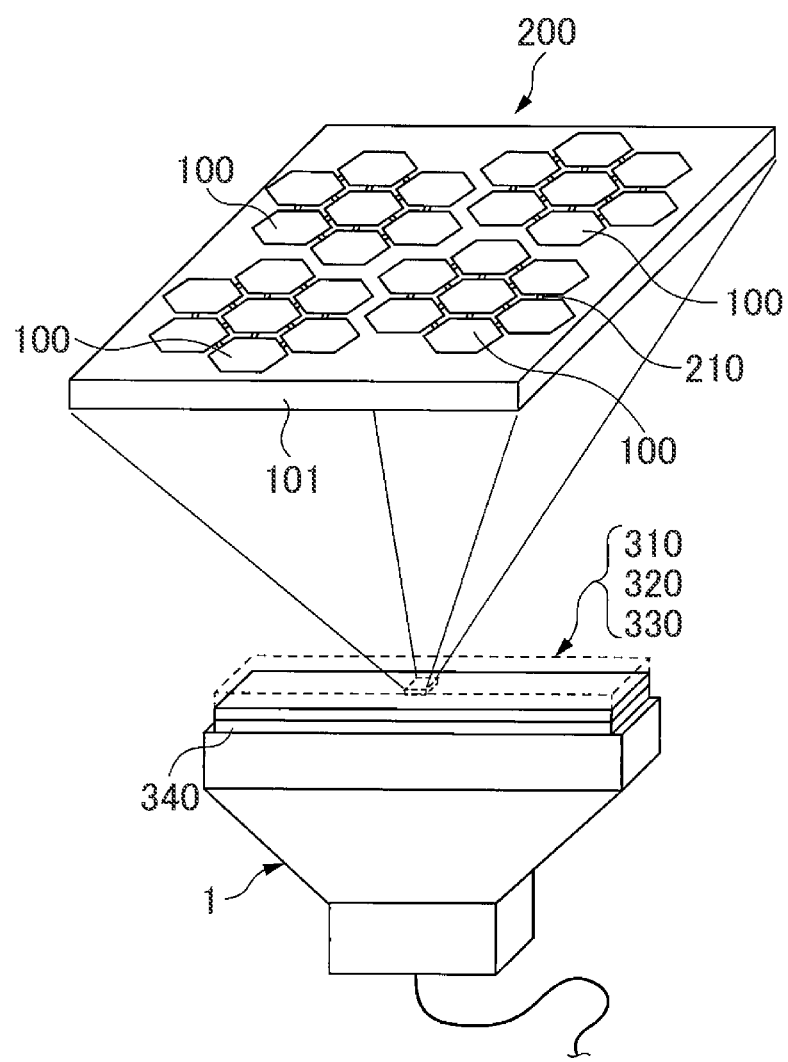
FIG. 3 is a perspective view showing an example of an ultrasonic transducer array and an example of an ultrasonic probe that are used for the ultrasonic image pickup apparatus according to the embodiment.

FIG. 3 is a perspective view showing an example of an ultrasonic transducer array and an example of an ultrasonic probe. As shown in FIG. 3, the ultrasonic transducer array 200 is included in the transmission/reception surface of the ultrasonic probe 1, and the ultrasonic transducer array 200 includes many cells (elements) each of which is a microscopic ultrasonic transducer 100 (with its horizontal width of 50 μm, for example) on the substrate 101, and every predefined number of cells are electrically connected to each other by a wire connection 210. Although the shape of a cell in FIG. 3 is hexagonal, the shape can be appropriately changed in accordance with the usage of the cell. Furthermore, the number of the ultrasonic transducers 100 is not limited to the number shown in FIG. 3, and it is conceivable that the cells of a larger number of ultrasonic transducers 100 are integratedly formed on a larger substrate using a semiconductor manufacturing technology and a printed-circuit board mounting technology.

Here, the arrangement of the ultrasonic transducers 100 shown in FIG. 3 is an example, and not only this faveolate arrangement but also another arrangement such as a rectangular arrangement can be adopted. In addition, as for a surface on which the ultrasonic transducers 100 is arranged, not only a plane surface but also a curved surface can be adopted, and further the shape of the curved surface can be a circular shape, a polygonal shape, or the like. Alternatively, the ultrasonic transducers 100 can be arranged in a linear line or in a curved line.

The ultrasonic probe 1 includes the transducer array 200 in which, for example, the plural ultrasonic transducers 100 arranged in paper strip-like forms are disposed in an array shape, or the plural ultrasonic transducers 100 arranged in fan-like forms are disposed in a convex shape.

Furthermore, as shown in FIG. 3, this ultrasonic probe 1 can be used in such a way that an acoustic lens 310 that is used for converging ultrasonic beams, an acoustic matching layer 320 used for matching the acoustic impedance of the ultrasonic transducers 100 with the acoustic impedance of a medium (test subject), and a conductive film 330 is disposed at the side of the medium (test subject) of ultrasonic transducers 100, and a backing material 340 that absorbs the propagation of ultrasonic waves is disposed at the backside (at the side opposite to the side of the medium).

<Images Obtained Using THI>

In the recent image diagnosis of superficial tissues performed using such an ultrasonic image pickup apparatus as described above, it is indispensable to obtain high-resolution images using THI (Tissue Harmonic Imaging), and in order to realize this, it becomes necessary to improve the S/Ns (Signal to Noise ratios) of images.

For example, although the PI (Pulse Inversion) method adopted in a related technology provides S/Ns higher than those of other methods in its principle, the PI method needs pairs of transmission sound pressure waveforms in which each pair is composed of two waveforms the shapes of which are the same but the signs of which are opposite, therefore the PI method cannot provide sound pressures sufficient for obtaining practical S/Ns in the operation principle of an ultrasonic transducer.

Alternatively, in a related technology, there is also a technology in which, in order to drive an ultrasonic transducer, an AC voltage to which a DC bias voltage is added is applied to a diaphragm layer (vibration film) to vibrate the diaphragm layer (vibration film). In this related technology, the vibration film is in a depressed state so that the depressed amount of the vibration film is 25% of the initial height of the void layer of the ultrasonic transducer due to the DC bias voltage, and the vibration film vibrates up and down with this depressed position as the center of the vibration. Although, if the DC bias voltage is increased, the depressed mount is increased, an electrostatic force between the fixed electrode 102 and the movable electrode 103 and the elastic restoring force of the vibration film 106 connected to the movable electrode 103 are not balanced with each other when the depressed amount exceeds a certain limit point, with the result that the vibration film 106, which cannot keep the depressed amount constant, collides with the fixed electrode 102. A phenomenon that causes this instability is referred to as an electrostatic pull-in, and a voltage that generates the electrostatic pull-in is referred to as a pull-in voltage. Because the DC bias voltage must not exceed this pull-in voltage, it is necessary to use the ultrasonic transducer with the depressed amount being 25% as mentioned above. Because an ultrasonic transducer 100 has an up-and-down asymmetric vibration characteristic, a sound pressure in the direction being swelled is only ⅓ of a sound pressure in the direction of the void layer being depressed in the case where the method according to the related technology being used.

For example, although, in the technology disclosed in the abovementioned Patent Literature 1, a high frequency pulse signal, on which a DC bias signal is superimposed, is applied to an ultrasonic vibrator, the movable range of a vibration film is not fully utilized because the voltage sign of the DC bias signal is simply switched between plus and minus, hence this technology is not suitable for realizing the S/N improvement of images using high sound pressures.

Therefore, this embodiment provides an ultrasonic image pickup apparatus in which problems raised by the related technologies including the technology disclosed by the abovementioned Patent Literature 1 are solved and the S/N improvement of images using high sound pressures is realized. The technical idea in this embodiment lies in an approach in which a waveform that generates a cancel error is intentionally transmitted at the time of transmission, and the low frequency components of the transmitted waveform are eliminated in the after-reception processing.

To put it concretely, first, with the use of a method which is obtained by adding a low frequency component to the PI (Pulse Inversion) method or the AMPI method (Amplitude Modulation Pulse Inversion Method: a kind of PI method in which sound pressure waveforms, the ratio of the amplitudes of which is not 1:1, is used), two transmission ultrasonic waves are transmitted respectively through two transmissions in which at least one of the two transmission ultrasonic waves (in other words, at least one kind of transmission ultrasonic wave of two or more kinds of transmission ultrasonic waves) has a low frequency component superimposed thereon. In this case, the low frequency component improves a transmission sound pressure by adjusting the position of the diaphragm layer (vibration film) at the time the vibration starts. This adjustment is executed for not improving the sensitivity of the vibration film but for widening the movable range of the vibration film so that a sound pressure in the direction of the vibration film being swelled can be properly output. Secondly, the low frequency component is not eliminated in addition processing performed after the reception of the transmission ultrasonic waves, and subsequently the low frequency component is eliminated by making the received transmission ultrasonic waves pass a highpass filter or a bandpass filter. Thirdly, although the ratio of sound pressure amplitudes can be set to an arbitrary value, it is desirable to output as large sound pressures as possible from the view point of S/N.

Hereinafter, the ultrasonic image pickup apparatus according to this embodiment will be described in detail on the basis of the technological idea in this embodiment.

<Transmission Processing, Reception Processing, and Signal Processing>

Figure 4:
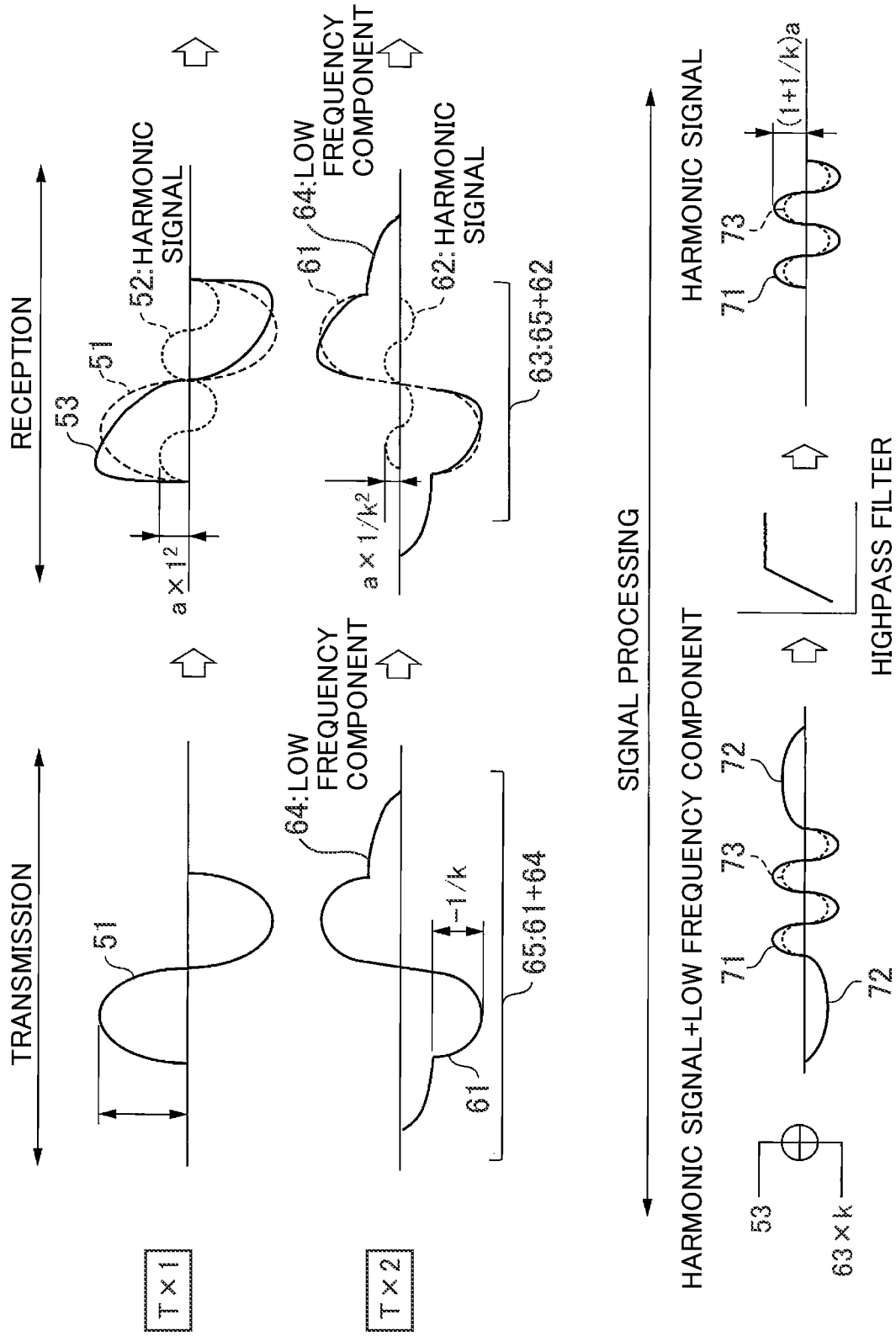
FIG. 4 is an explanatory diagram schematically showing examples of the flows of transmission, reception, and signal processing in the ultrasonic image pickup apparatus according to the embodiment.

FIG. 4 is an explanatory diagram schematically showing examples of the flows of transmission, reception, and signal processing in the ultrasonic image pickup apparatus according to the embodiment. In the ultrasonic image pickup apparatus according to the embodiment, a method in which a low frequency component is added to the AMPI method is used.

As shown above (in FIG. 2), in the ultrasonic image pickup apparatus according to this embodiment, waveform control is executed on a transmission signal by the control unit 12, and after going through the transmission beam former 8, the D/A converter 6, and the transmission amplifier 3, the transmission signal is applied as a driving voltage to an ultrasonic transducer 100 of the ultrasonic probe 1 in such a state that a desired waveform is set to the transmission signal.

The driving voltage applied to the ultrasonic transducer 100 is applied between the fixed electrode 102 and the movable electrode 103 in the ultrasonic transducer 100, and the movable electrode 103 is displaced by an electrostatic force caused by the driving voltage. At this time, the vibration film (diaphragm layer) 106 connected to the movable electrode 103 is also displaced. As a result, the displacement of the vibration film 106 is radiated as a sound pressure to a medium that resides at the front face such as a living organism.

After going through the reception amplifier 4, the A/D converter 7, and the reception former 9, a reception signal corresponding to the sound pressure radiated to the medium is converted into an image signal in the signal processing unit 13, and the image signal is displayed on the display unit 15 via the scan converter 14.

In the ultrasonic image pickup apparatus according to this embodiment, an ultrasonic wave is transmitted by applying a DC bias voltage and an AC driving voltage between the fixed electrode 102 and the movable electrode 103 of an ultrasonic transducer 100 as the driving voltage to the ultrasonic transducer 100. At this time, the vibration film 106 of the ultrasonic transducer 100 is displaced if the driving voltage is applied. This displacement of the vibration film 106 becomes a sound pressure. Two or more kinds of ultrasonic waveforms which have different signs, amplitudes, or phases from each other for one scanning line are transmitted as a sound pressure on a medium (test subject). The reflection signal corresponding to the transmission of this sound pressure is received, and the image of the internal tissue of the test subject (the tissue of the living organism) is picked up through these transmission and reception operations.

In other words, the ultrasonic image pickup apparatus according to this embodiment includes the transmission/reception control unit that transmits an ultrasonic wave by applying a DC bias voltage and an AC driving voltage between the electrodes of the ultrasonic transducer 100 and picks up an image by transmitting and receiving two or more kinds of ultrasonic waveforms which have different signs, amplitudes, or phases from each other for one scanning line. This transmission/reception unit is a part of the ultrasonic image pick up apparatus including the control unit 12, the transmission beam former 8, and the reception beam former 9.

<<Transmission>>

When a sound pressure is transmitted to a medium (test subject), two or more kinds of transmission ultrasonic waves are transmitted. In this embodiment, Tx1 and Tx2 are shown as examples of two kinds of transmission ultrasonic waves. At least one kind of these two transmission ultrasonic waves, for example, Tx2 is a voltage waveform obtained by adding a high frequency pulse waveform 61 and a low frequency waveform 64 and it is used as an AC driving voltage. In FIG. 4, the high frequency pulse waveform 61 of the transmission ultrasonic wave Tx2 is shown as a waveform obtained by executing amplitude modulation and pulse inversion on the high frequency pulse waveform 51 of the transmission ultrasonic wave Tx1, with the result that the high frequency pulse waveform is shown with "$-1/k$ ($k$=a coefficient according to the amplitude of a transmission sound pressure) in FIG. 4.

In addition, it will be assumed that the low frequency waveform 64 of the transmission ultrasonic wave Tx2 is a low frequency waveform that has a longer cycle than that of the high frequency pulse waveform 61 and has such a voltage amplitude as makes the sum of the amplitude of its voltage and the DC bias voltage equal or smaller than a pull-in voltage and that smoothly changes in accordance with a trapezoidal wave, a cosine function, an nth power of cosine, a Gaussian function or the like. The pull-in voltage is a critical voltage value that makes an electrostatic force between the fixed electrode 102 and the movable electrode 103 and an elastic restoring force of the vibration film 106 connected to the movable electrode 103 imbalanced with each other, and if the pull-in voltage is exceeded, the vibration film cannot be kept within the void, hence the vibration film get into touch with the lower surface.

Another kind of the transmission ultrasonic waves Tx1 and Tx2, for example, Tx1 is a high frequency pulse waveform, and it is used as an AC driving voltage. In FIG. 4, the amplitude of the high frequency pulse waveform 51, which is transmission ultrasonic wave Tx1, is represented by "1".

In such a way, a sound pressure waveform including a first transmission ultrasonic wave Tx1 with the maximum amplitude and a second transmission ultrasonic wave Tx2 with the minimum amplitude is transmitted as a combination of two or more kinds of transmission ultrasonic waves. Here, it will be assumed that the ratio of the sound pressure amplitude of the first transmission ultrasonic wave Tx1 to that of the second transmission ultrasonic wave Tx2 is 1 to ⅓ or larger, or 1 to 1 or smaller, and plus and minus of sign are switched.

<<Reception>>

In the reception of the transmission ultrasonic wave Tx2 via a medium (test subject), as shown in FIG. 4, a waveform 63 obtained by adding the transmitted sound pressure waveform 61 and the waveform 62 of a secondary harmonic component generated by a nonlinear effect due to the propagation of a sound wave through the medium is received. In this case, because the magnitude of the second harmonic component generated due to the medium is proportional to the square of the magnitude of the transmitted sound pressure waveform, the second harmonic component 62 included in the reception waveform 63 of the transmitted ultrasonic wave Tx2 is shown in FIG. 4 as "$a \times 1/k^2$ ($a$–a coefficient depending on the medium, $k$–a coefficient according to the amplitude of a transmission sound pressure".

On the other hand, in the reception of the transmission ultrasonic wave Tx1 via the medium (test subject), as shown in FIG. 4, a waveform 53 obtained by adding the transmitted sound pressure waveform 51 and the waveform 52 of a secondary harmonic component generated by a nonlinear effect due to the propagation of a sound wave through the medium is received. At this time, because the magnitude of the second harmonic component generated due to the medium is proportional to the square of the magnitude of the transmitted sound pressure waveform, the second harmonic component 52 included in the reception waveform 53 of the transmitted ultrasonic wave Tx1 is shown in FIG. 4 as "$a \times 1^2$". Here, "$a$" is a coefficient obtained as a result of a nonlinear effect and an attenuation effect being into consideration. The reason why "$a$" is multiplied by $1^2$ is that a harmonic component is generated not linearly proportionally to a transmitted sound wave but it is generated nonlinearly proportionally (in this case, it is assumed that the harmonic component is generated approximately proportionally to the square). In this case, although it is assumed that the harmonic component is generated proportionally to the square for descriptive purposes, it is also possible to assume that the harmonic component is generated proportionally to the nth power (n is any number) of the transmitted sound wave such as the 3rd power or 2.5th power of the transmitted sound wave. Furthermore, there can be various modes of harmonic waves other than the second harmonic wave such as the third harmonic wave, the fourth harmonic wave, the difference frequency wave, and the like. In this case, although the second harmonic wave is taken for an example for descriptive purposes, similar discussions can hold about other modes of harmonic waves.

<<Signal Processing>>

Signal processing is performed on the reception waveforms of these transmission ultrasonic waves Tx2 and Tx1 in order for these transmission ultrasonic waves Tx2 and Tx1 to be converted into image signals. First, in FIG. 4, in order to align the amplitude of the transmission sound pressure waveform 51 of Tx1 and the amplitude of the transmission sound pressure waveform 52 of Tx2, multiplication is executed on the reception waveform 63 of the received transmission ultrasonic wave Tx2 (the multiplier is shown as "1/k"). Through this multiplication processing, the second harmonic component generated in Tx2 becomes "k×a/k²". On the other hand, the second harmonic component 52 of the reception waveform 53 of the transmission ultrasonic wave Tx1 is set to remain "a×1²". By performing addition processing on these reception waveform 63 and reception waveform 53, because the sound pressure waveform 51 transmitted in Tx1 and the sound pressure waveform 61 transmitted in Tx2 have signs opposite to each other, these waveforms cancel each other, and as a result, this addition processing generates a waveform obtained by adding a harmonic signal waveform 71 obtained by adding "k×a/k²" attributable to the second harmonic component in Tx2 and "a×1²" attributable to the second harmonic component in Tx1 and a low frequency waveform 72 derived from the low frequency waveform 64 transmitted in Tx2. The waveform obtained by adding the above harmonic signal waveform 71 and the low frequency waveform 72 is depicted in a solid line, and this waveform is a waveform obtained by adding the waveform corresponding to the transmission ultrasonic wave Tx2 and the waveform corresponding to the transmission ultrasonic wave Tx1. Here, a waveform 73 depicted in a dashed line is a waveform corresponding to the transmission ultrasonic wave Tx1.

Subsequently, the waveform obtained by adding the above harmonic signal waveform 71 and the low frequency waveform 72 are gotten through a highpass filter or a bandpass filter, so that the low frequency component of the waveform is eliminated. With this, the harmonic signal waveform 71 from which the low frequency component is eliminated can be obtained. In FIG. 4, the harmonic signal waveform 71 is shown by "(1+1/k)a". For example, if k=2, the harmonic signal waveform 71 becomes "(3/2)a". This harmonic signal waveform 71 is further converted into an image signal.

In the signal processing performed on the basis of the reception waveforms of these transmission ultrasonic waves Tx2 and Tx1, after the ultrasonic waves are transmitted plural times, pieces of processing are performed on the respective received ultrasonic wave signals. In this case, as described above, the transmission ultrasonic wave Tx2 is added after the transmission ultrasonic wave Tx2 is multiplied by the coefficient "k" subject to the amplitude of the corresponding transmission sound pressure. Subsequently, the low frequency component of the reception signal is eliminated by the highpass filter or the bandpass filter, so that the harmonic signal waveform 71 can be obtained.

<Displacement of Vibration Film>

Figure 5:
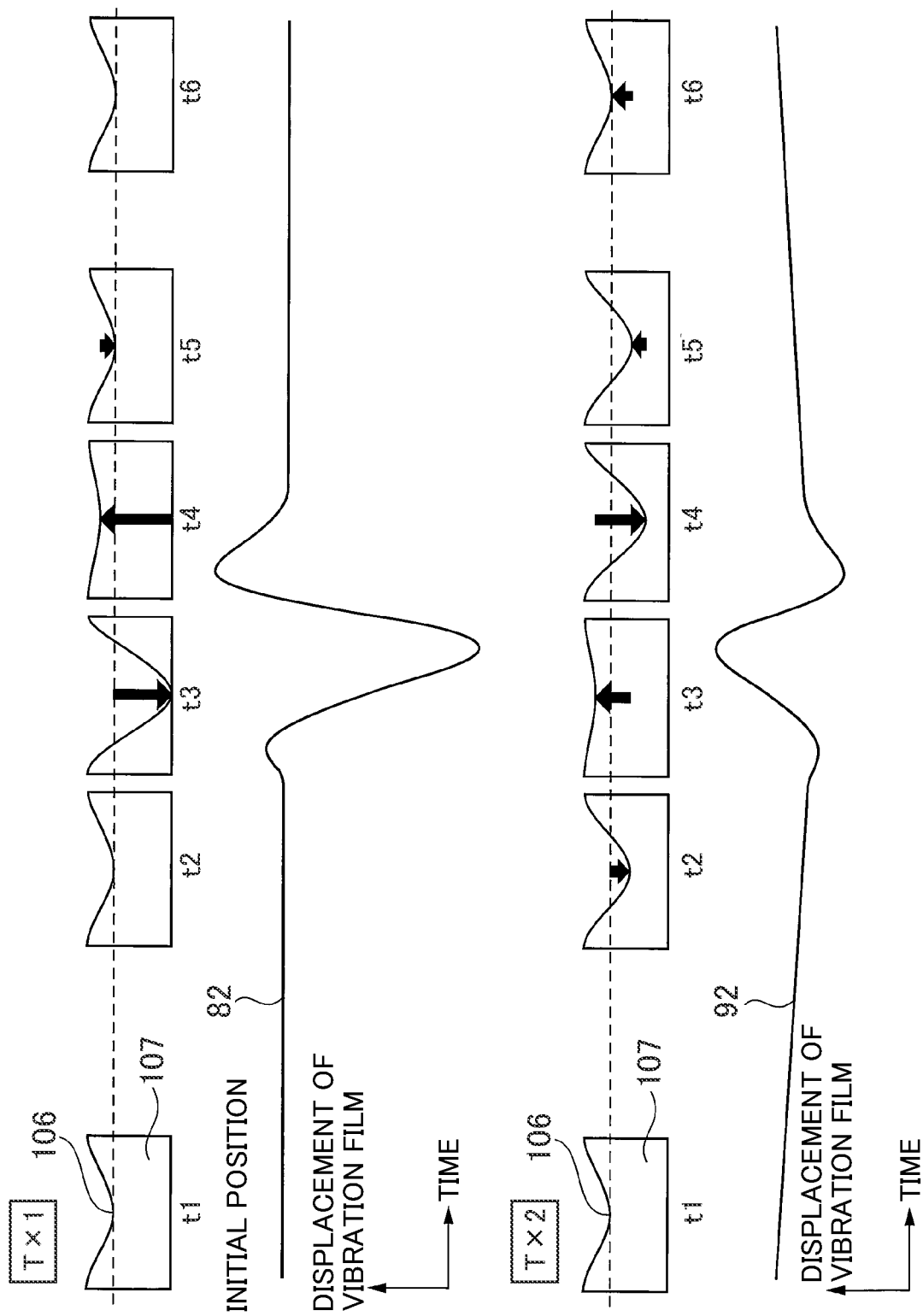
FIG. 5 is an explanatory diagram showing examples of the displacements of a vibration film in the ultrasonic image pickup apparatus according to the embodiment.

FIG. 5 is an explanatory diagram showing examples of the displacements of a vibration film in the ultrasonic image pickup apparatus according to the embodiment. FIG. 5 shows the displacements of the vibration film 106 (the diaphragm layer shown in FIG. 2) of waveforms 82 and 92 corresponding to the transmission ultrasonic waves Tx1 and Tx2 respectively at the times t1 to t6. In FIG. 5, arrows showing the displacements of the vibration film 106 show the displacement amounts of the vibration film 106, and the vibration film 106 is displaced in the direction shown by each arrow, and the length of each arrow is proportional to the magnitude of the displacement amount. In addition, the waveforms 82 and 92 shown in FIG. 5 are respectively waveforms 82 and 92 that show the displacements of the vibration film 106 respectively shown in after-mentioned FIG. 6(b) and FIG. 7(b).

In FIG. 5, the time t1 is the initial position of the vibration film 106. At the initial position, in each case of Tx1 and Tx2n, the vibration film 106 is in a depressed state so that the depressed amount of the vibration film 106 is 25% of the height of the void layer 107.

At the time t2 following the time 1, the position of the vibration film 106 remains in the state of the initial position in the case of Tx1. On the other hand, in the case of Tx2, because the vibration film 106 is slowly displaced, the vibration film 106 goes into a state where the vibration film 106 is more depressed than the state of the initial position. In other words, in the case of Tx2, the vibration film 106 is depressed in advance more deeply than the state of the initial position to enlarge the displacement amount of the vibration film 106. A sound pressure corresponding to the low frequency component 64 shown in FIG. 4 is generated in proportion to this displacement amount of the vibration film 106.

At the time t3 following the time t2, in the case of Tx1, the vibration film 106 is set in a state where the vibration film 106 is depressed by 100% of the height of the void layer 107 from the state of the initial position. On the other hand, in the case of Tx2, the vibration film 106 is displaced from the above state depressed in advance more deeply than the initial position to the state where the vibration film 106 is more swelled than in the state of the initial position.

At the time t4 following the time t3, in the case of Tx1, the vibration film 106 is displaced from the state where the vibration film 106 is depressed by about 100% of the height of the void layer 107 to the state where the vibration film 106 is more swelled than in the state of the initial position. On the other hand, in the case of Tx2, the vibration film 106 is displaced from the state where the vibration film 106 is more swelled than in the state of the initial position to the state where the vibration film 106 depressed more deeply than in the state of the initial position.

At the time t5 following the time t4, in the case of Tx1, the vibration film 106 is displaced from the state where the vibration film 106 is more swelled than in the state of the initial position to the state of the initial position. On the other hand, in the case of Tx2, the vibration film 106 is displaced from the state depressed more deeply than the initial position to a position nearer to the initial position.

At the time t6 following the time t5, in the case of Tx1, the vibration film 106 is kept in the state of the initial position. On the other hand, in the case of Tx2, the vibration film 106 is displaced from the state near to the initial position to the state of the initial position.

In this way, by adding the low frequency component to the transmission ultrasonic wave Tx2, it becomes possible to vibrate the vibration film 106 at high frequency vibrations (at the times t3 and t4) using the height of the void layer as much as possible, hence a high sound pressure can be obtained. Furthermore, because the low frequency component displaces the vibration film 106 at a frequency vibration lower than the above high frequency vibrations (at the times t3 and t4), a generated ultrasonic wave due to the low frequency component becomes a low frequency/low sound pressure ultrasonic wave, hence it becomes easy to eliminate the low frequency component at the signal processing performed after the reception. This is because the amplitude of a sound pressure is proportional to the velocity of the relevant vibration film.

<Driving Voltage to Ultrasonic Transducer, Displacement of Vibration Film, and Sound Pressure on Medium>

Figure 6A:
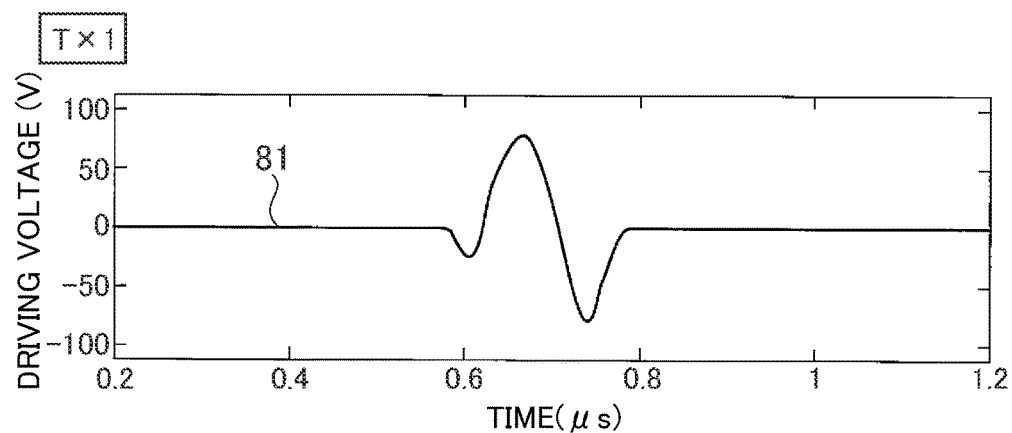
FIGS. 6(*a*) to 6(*c*) are explanatory diagrams showing examples of the driving voltage, the displacement of the vibration film, and a sound pressure on the medium of the ultrasonic transducer in the ultrasonic image pickup apparatus according to the embodiment.
Figure 6B:
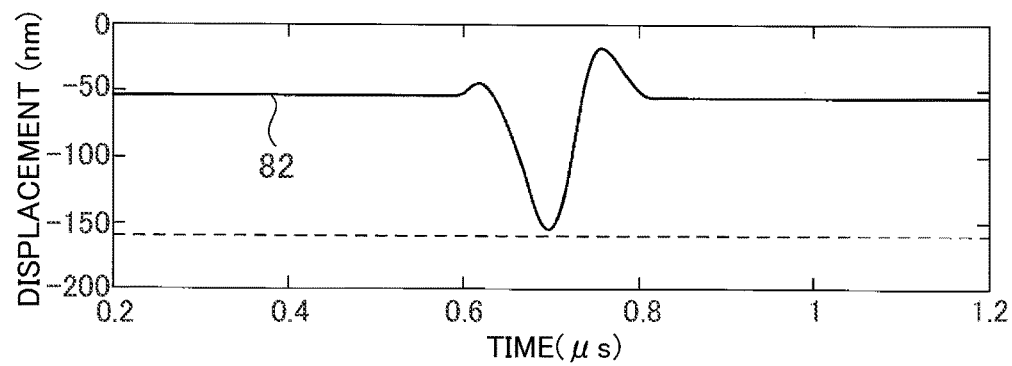
Figure 6C:
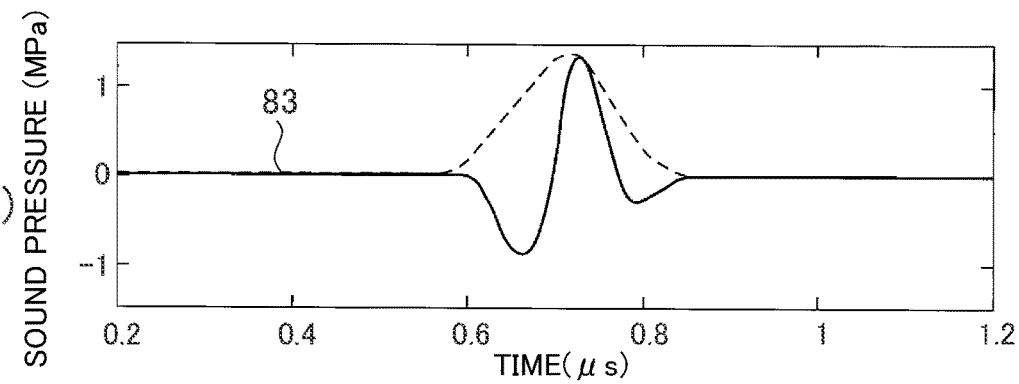

FIG. 6(a) to FIG. 6(c) and FIG. 7(a) to FIG. 7(c) are respectively explanatory diagrams showing examples of driving voltages applied to the ultrasonic transducer, the displacements of the vibration film of the ultrasonic transducer, and sound pressures on the medium of the ultrasonic transducer in the ultrasonic image pickup apparatus according to the embodiment. FIG. 6(a) to FIG. 6(c) correspond to the transmission ultrasonic wave Tx1, and FIG. 7(a) to FIG. 7(c) correspond to the transmission ultrasonic wave Tx2. FIG. 6(a) shows a driving voltage (V) to the ultrasonic transducer vs. time (μs), FIG. 6(b) shows the displacement (nm) of the vibration film vs. time (μs), and FIG. 6(c) shows a sound pressure (MPa) on the medium vs. time (μs) for the transmission ultrasonic waves Tx1 and Tx2 respectively.

Figure 7A:
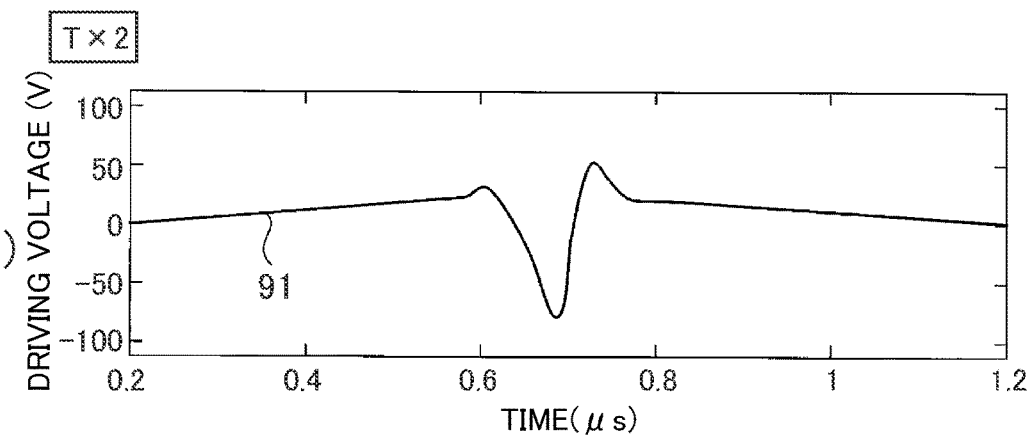
FIGS. 7(a) to 7(c) are explanatory diagrams showing examples of the driving voltage, the displacement of the vibration film, and a sound pressure on the medium of the ultrasonic transducer in the ultrasonic image pickup apparatus according to the embodiment.
Figure 7B:
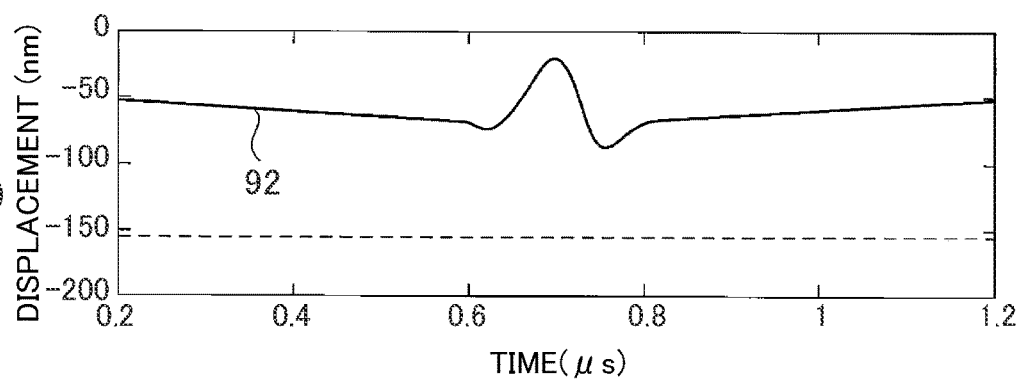

In order to obtain the displacements of the vibration film 106 respectively corresponding to the transmission ultrasonic waves Tx1 and Tx2 as shown in FIG. 5, a voltage with a waveform 81 shown in FIG. 6(a) and a voltage with a waveform 91 shown in FIG. 7(a) are applied to the ultrasonic transducer 100 respectively as driving voltages. In the driving voltage with the waveform 81 shown in FIG. 6(a), the driving voltage is kept 0 V until time becomes 0.6 μs, decreased to −25 V when time is 0.6 μs, increased to +75 V when time is 0.67 μs, decreased to −75 V when time is 0.74 μs, and kept 0 V after time becomes 0.8 μs. In the driving voltage with the waveform 91 shown in FIG. 7(a), the driving voltage is gradually increased from 0 V to +25 V until time becomes 0.6 μs, increased to +30 V when time is 0.6 μs, decreased to −75 V when time is 0.69 μs, increased to +50 V when time is 0.71 μs, and gradually decreased from +25 V to 0V after time becomes 0.8 μs.

Consequently, the above driving voltages applied to the ultrasonic transducer 100 are respectively applied between the fixed electrode 102 and the movable electrode 103 in the ultrasonic transducer 100, hence the movable electrode 103 is displaced by electrostatic forces respectively. At this time, the vibration film 106 connected to the movable electrode 103 is also displaced respectively according to the displacement of the waveform 82 shown in FIG. 6(b) and the displacement of the waveform 92 shown in FIG. 7(b). In the displacement of the waveform 82 shown in FIG. 6(b), the displacement is kept −55 nm until time becomes 0.6 μs, becomes −45 nm when time is 0.6 μs, becomes −150 nm when time is 0.7 μs, becomes −25 nm when time is 0.75 μs, and the displacement is kept −55 nm after time becomes 0.8 μs. In the displacement of the waveform 92 shown in FIG. 7(b), the displacement is gradually changed from −50 nm to −70 nm until time becomes 0.6 μs, becomes −75 nm when time is 0.6 μs, becomes −20 nm when time is 0.7 μs, becomes −80 nm when time is 0.75 μs, and the displacement is gradually changed from −70 nm to −50 nm after time becomes 0.8 μs.

Figure 7C:
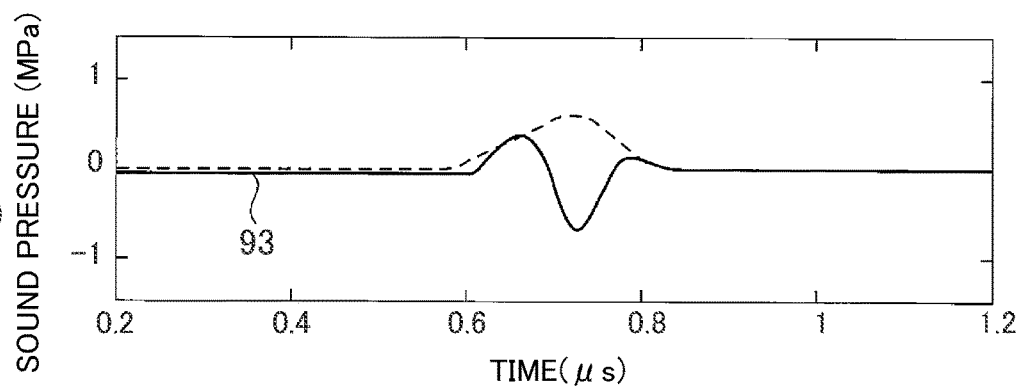

Consequently, the sound pressure with the waveform 83 shown in FIG. 6(c), and the sound pressure with the waveform 93 shown in FIG. 7(c) are respectively radiated to a medium that resides at the front face of the vibration film 106 such as a living organism. In the case of the sound pressure of the waveform 83 shown in FIG. 6(c), the sound pressure is kept 0 MPa until time becomes 0.6 μs, becomes −0.9 MPa when time is 0.66 μs, becomes +1.2 MPa when time is 0.73 μs, becomes −0.3 MPa when time is 0.8 μs, and the sound pressure is kept 0 MPa after time becomes 0.85 μs. In the case of the sound pressure of the waveform 93 shown in FIG. 7(c), the sound pressure is kept 0 MPa until time becomes 0.6 μs, becomes +0.4 MPa when time is 0.66 μs, becomes −0.7 MPa when time is 0.73 μs, becomes +0.1 MPa when time is 0.78 μs, and the sound pressure is kept 0 MPa after time becomes 0.8 μs.

<Feature of Transmission Ultrasonic Wave>

Figure 8:
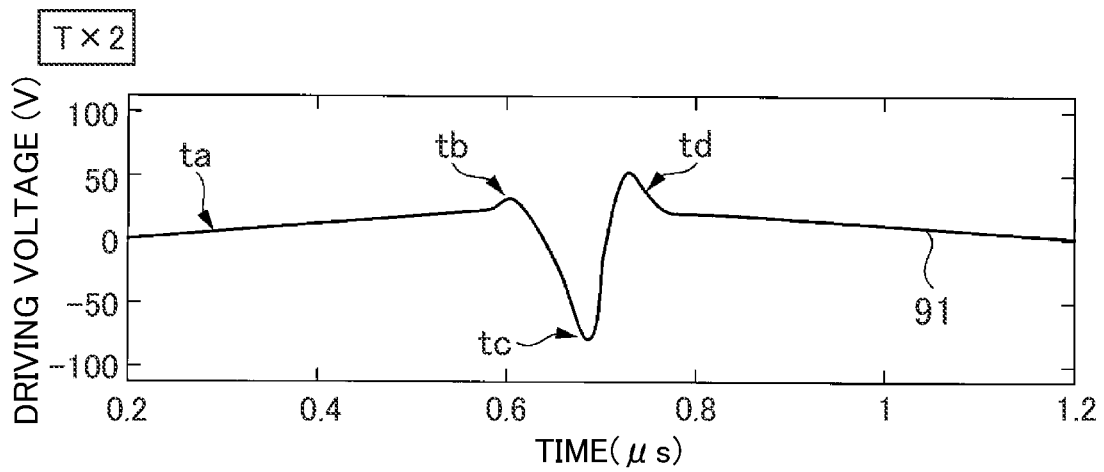
FIG. 8 is an explanatory diagram showing an example of the driving voltage applied to the ultrasonic transducer in response to a transmission ultrasonic wave in the ultrasonic image pickup apparatus according to the embodiment.
Figure 9:
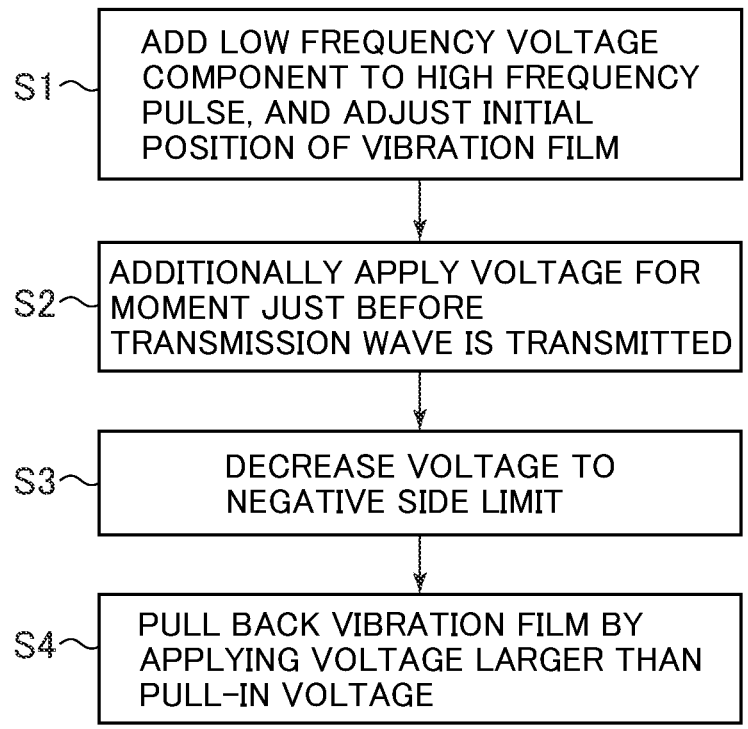
FIG. 9 is an explanatory diagram showing an example of a procedure for applying the driving voltage to the ultrasonic transducer in response to the transmission ultrasonic wave in the ultrasonic image pickup apparatus according to the embodiment.

FIG. 8 and FIG. 9 are explanatory diagrams showing an example of the features of the transmission ultrasonic wave in the ultrasonic image pickup apparatus according to the embodiment. FIG. 8 shows the driving voltage (V) applied to the ultrasonic transducer corresponding to the transmission ultrasonic wave Tx2, and FIG. 9 shows a procedure for applying the driving voltage. A waveform 91 shown in FIG. 8 is the waveform 91 showing the driving voltage of the abovementioned FIG. 7(a). Here, it will be assumed that a positive DC voltage is applied to the electrode at the side of the vibration film (equivalent to the movable electrode 103 shown in FIG. 2), and the voltage shown in FIG. 8 is also applied to the electrode at the side of the vibration film. However, the DC voltage and the AC voltage may be applied to the electrode at the side of the lower layer (equivalent to the fixed electrode 102 shown in FIG. 2) with a thought that the electrode at the side of the lower layer is a positive terminal.

As a driving voltage to the ultrasonic transducer corresponding to the transmission ultrasonic wave Tx2 shown in FIG. 8, the voltage waveform 91 having the following feature is applied in accordance with the procedure shown in FIG. 9.

First, a low frequency voltage component is added to a high frequency pulse at the timing ta to adjust the initial position of the vibration film 106 (S1). It will be assumed that this low frequency voltage component is such a voltage component as makes the total voltage of its voltage and the DC bias equal or smaller than a pull-in voltage, and that the rising waveform of this low frequency voltage component smoothly changes in accordance with a trapezoidal wave, a cosine function, an nth power of cosine, a Gaussian function or the like.

Next, at the timing tb, which is a timing a predefined time after the timing ta, a voltage is additionally applied just before the transmission ultrasonic wave Tx2 is transmitted (S2). A voltage exceeding the pull-in voltage is applied as this voltage to pull back the vibration film 106.

Next, at the timing tc, which is a timing a predefined time after the timing tb, the voltage is decreased to a negative side limit (S3).

Subsequently, at the timing td, which is a timing a predefined time after the timing tc, a voltage exceeding the pull-in voltage is applied to pull back the vibration film 106 (S4). In this case, by temporarily applying the voltage exceeding the pull-in voltage, a large electrostatic force is instantaneously generated in the vibration film, hence the vibration film 106 is quickly pulled back to its initial position. Here, a time period during which the voltage exceeding the pull-in voltage is applied is limited to a time period within which the vibration film does not come into contact with the lower surface.

In other words, in the case of the transmission ultrasonic wave Tx2, a precedent positive voltage pulse (a part shown at the timing tb), one or more main pulses each of which is composed of a positive voltage or a negative voltage (FIG. 8 shows an example of one main pulse) (a part shown at the timing tc), and a subsequent positive voltage pulse (a part shown at the timing td) are continuously output in terms of time as a high frequency pulse waveform. In this case, the total of the maximum voltage value of the precedent pulse and the DC bias voltage is set to exceed the pull-in voltage of the ultrasonic transducer 100. In addition, of the plural main pulses, a main pulse that is output just after the precedent pulse is composed of a negative voltage. Furthermore, the total of the maximum voltage value of the precedent pulse and the DC bias voltage is set to exceed the pull-in voltage of the ultrasonic transducer 100.

According to the above-described ultrasonic image pickup apparatus according to this embodiment, the S/N improvement of images with the use of high sound pressures can be realized. To put it concretely, the ultrasonic image pickup apparatus according to this embodiment is characterized in that a waveform that intentionally generates a cancel error is transmitted at the time of transmission, and the low frequency components of the received waveform are eliminated in the after-reception processing, hence in both cases of the transmission ultrasonic waves Tx1 and Tx2 being transmitted, the mechanical movable range of the ultrasonic transducer 100 can be maximally leveraged. Due to the above advantageous effect, a transmission sound pressure can be set to a high sound pressure, so that the improvement of the S/N of images can be realized.

Although the present invention achieved by the inventors has been explained concretely on the basis of the embodiment, the present invention is not limited to the embodiment described above, and it goes without saying that various changes can be made without deviating from the gist of the present invention.

In addition, the present invention is not limited to the above embodiment, and the present invention may include various kinds of modification examples. For example, the above embodiment has been described in detail in order to explain the present invention in an easily understood manner, and the present invention is not necessarily limited to an ultrasonic image pickup apparatus including all the configurations that have been described so far.

Furthermore, a part of the configuration of one embodiment can be replaced with a part of the configuration of another embodiment, and it is also possible to add the configuration of one embodiment to the configuration of another embodiment. In addition, a part of the configuration of each embodiment may be made by adding, deleting, or replacing a part of another configuration.

LIST OF REFERENCE SIGNS

1 . . . Ultrasonic Prove, 2 . . . Transmission/Reception Switching Switch, 3 . . . Transmission Amplifier, 4 . . . Reception Amplifier, 5 . . . DC Power Supply, 6 . . . D/A Converter, 7 . . . A/D Converter, 8 . . . Transmission Beam Former, 9 . . . Reception Beam Former, 10 . . . Power Supply, 11 . . . Voltage Limiter, 12 . . . Control Unit, 13 . . . Signal Processing Unit, 14 . . . Scan Converter, 15 . . . Display Unit, 16 . . . User Interface, 51, 52, 53, 61, 62, 63, 64, 65, 71, 72, 73 . . . Waveform, 81, 82, 83, 91, 92, 93 . . . Waveform, 100 . . . Ultrasonic Transducer, 101 . . . Substrate, 102 . . . Fixed Electrode, 103 . . . Movable Electrode, 104 . . . Insulating Film, 105 . . . Insulating Film, 106 . . . Diaphragm Layer (Vibration Film), 107 . . . Void Layer, 108 . . . Supporting Wall, 200 . . . Ultrasonic Transducer Array, 210 . . . Wire Connection, 310 . . . Acoustic Lens, 320 . . . Acoustic Matching Layer, 330 . . . Conductive Film, 340 . . . Backing Material

The invention claimed is:

1. An ultrasonic image pickup apparatus using an electrostatic capacity type micro-machined ultrasonic transducer as an ultrasonic probe, the ultrasonic image pickup apparatus comprising a transmission/reception control unit that:
   transmits an ultrasonic wave by applying a DC bias voltage and an AC driving voltage between electrodes of the electrostatic capacity type micro-machined ultrasonic transducer; and
   picks up an image by transmitting and receiving a first transmission ultrasonic waveform and a second transmission ultrasonic waveform for one scanning line,
   wherein the first transmission ultrasonic waveform is a high frequency waveform, and
   wherein the second transmission ultrasonic waveform is formed by:
   a high frequency waveform that has different sign, amplitude or phase from the high frequency waveform of the first transmission ultrasonic waveform; and
   a low frequency waveform that has a longer time duration than that of the high frequency waveforms of the first transmission ultrasonic waveform and the second transmission ultrasonic waveform and is generated by the ultrasonic probe when a low frequency voltage waveform is applied to the ultrasonic probe, the low frequency voltage waveform has a voltage amplitude that makes the total voltage of the low frequency voltage waveform and the DC bias voltage equal to or smaller than a pull-in voltage of the probe, the low frequency waveform smoothly changing in accordance with an arbitrary function.

2. The ultrasonic image pickup apparatus according to claim 1,
   wherein, after transmitting ultrasonic waves a plurality of times, the ultrasonic image pickup apparatus multiplies respective received ultrasonic signals by coefficients corresponding to the transmission sound pressure amplitudes relevant to the respective received ultrasonic wave signals, adds these ultrasonic signals, and then eliminates a low frequency component of the received ultrasonic signals.

3. The ultrasonic image pickup apparatus according to claim 1,
   wherein the ultrasonic image pickup apparatus transmits a sound pressure wave including the first transmission ultrasonic waveform that has a maximum amplitude and the second transmission ultrasonic waveform that has a minimum amplitude as the transmission ultrasonic wave; and
   wherein the ratio of the sound pressure amplitude of the first transmission ultrasonic wave and the sound pressure amplitude of the second transmission ultrasonic wave is 1 to 1 or smaller, and plus and minus signs are switched.

4. The ultrasonic image pickup apparatus according to claim 1,
   wherein the ultrasonic image pickup apparatus outputs a precedent positive voltage pulse, one or a plurality of main pulses each of which is composed of a positive voltage or a negative voltage, and a subsequent positive voltage pulse continuously in terms of time as the high frequency pulse waveform; and
   wherein the total of the voltage maximum value of the precedent pulse and the DC bias voltage exceeds the pull-in voltage of the electrostatic capacitor type micro-machined ultrasonic transducer.

5. The ultrasonic image pickup apparatus according to claim 4,
wherein a main pulse among the plurality of main pulses that is output just after the precedent pulse is composed of a negative voltage.

6. The ultrasonic image pickup apparatus according to claim 4,
wherein the total of the voltage maximum value of the subsequent pulse and the DC bias voltage exceeds the pull-in voltage of the electrostatic capacitor type micro-machined ultrasonic transducer.

7. The ultrasonic image pickup apparatus according to claim 1,
wherein the low frequency waveform varies in accordance with an arbitrary function which is a trapezoidal wave, a cosine function, an nth power of cosine, or a Gaussian function.

8. An ultrasonic image pickup apparatus using an electrostatic capacity type micro-machined ultrasonic transducer as an ultrasonic probe, the ultrasonic image pickup apparatus comprising a transmission/reception control unit that transmits first and second ultrasonic transmission waveforms respectively through two transmissions to the electrostatic capacitor type micro-machined ultrasonic transducer,
wherein the first transmission ultrasonic waveform is a high frequency waveform, and
wherein the second transmission ultrasonic waveform is formed by:
a high frequency waveform; and
a low frequency waveform that has a longer time duration than that of the high frequency waveforms of the first transmission ultrasonic waveform and the second transmission ultrasonic waveform and is generated by the ultrasonic probe when a low frequency voltage waveform is applied to the ultrasonic probe, the low frequency voltage waveform has a voltage amplitude that makes the total voltage of the low frequency voltage waveform and a DC bias voltage equal to or smaller than a pull-in voltage of the probe, the low frequency waveform smoothly changing in accordance with an arbitrary function as an AC driving voltage, the voltage waveform being applied to adjust an initial position of a vibration film of the electrostatic capacitor type micro-machined ultrasonic transducer.

9. The ultrasonic image pickup apparatus according to claim 8,
wherein the low frequency component is eliminated by means of a highpass filter or a bandpass filter after addition processing is performed on the transmission waveforms that have been transmitted through the two transmissions and received.

10. The ultrasonic image pickup apparatus according to claim 8,
wherein, the ratio of the sound pressure amplitude of the first transmission ultrasonic waveform and the sound pressure amplitude of the second transmission ultrasonic waveform is 1 to 1 or smaller, and plus and minus signs are switched.

11. The ultrasonic image pickup apparatus according to claim 8,
wherein a voltage that exceeds the pull-in voltage of the electrostatic capacitor type micro-machined ultrasonic transducer is applied before each of the first and second transmission ultrasonic waveforms is transmitted.

12. The ultrasonic image pickup apparatus according to claim 11,
wherein, after a voltage exceeding the pull-in voltage is applied, the voltage is decreased to a negative side limit.

13. The ultrasonic image pickup apparatus according to claim 12,
wherein, after the voltage is decreased to the negative side limit, the vibration film is pulled back by applying a voltage larger than the pull-in voltage.

14. The ultrasonic image pickup apparatus according to claim 13,
wherein the low frequency component is eliminated by means of a highpass filter or a bandpass filter after addition processing is performed on the transmission waveforms that have been transmitted through the two transmissions and received, and
wherein the voltage amplitude of the second transmission ultrasonic waveform is multiplied by a coefficient before being added to the first transmission ultrasonic waveform.

\* \* \* \* \*